United States Patent [19]

Kotliar

[11] Patent Number: 5,799,652
[45] Date of Patent: Sep. 1, 1998

[54] HYPOXIC ROOM SYSTEM AND EQUIPMENT FOR HYPOXIC TRAINING AND THERAPY AT STANDARD ATMOSPHERIC PRESSURE

[75] Inventor: Igor K. Kotliar, New York, N.Y.

[73] Assignee: Hypoxico Inc., New York, N.Y.

[21] Appl. No.: 505,621

[22] Filed: Jul. 21, 1995

Related U.S. Application Data

[63] Continuation-in-part of Ser. No. 445,677, May 22, 1995.

[51] Int. Cl.$^6$ .......................... A63B 23/18; A62B 7/00; A62B 9/00; G05B 1/00
[52] U.S. Cl. .......................... 128/205.11; 128/200.24; 128/202.12; 128/205.26; 482/13
[58] Field of Search .......................... 128/200.24, 202.12, 128/202.13, 205.11, 205.12, 205.26; 482/13

[56] References Cited

U.S. PATENT DOCUMENTS

| | | | |
|---|---|---|---|
| 365,067 | 6/1887 | Harris | 128/202.12 |
| 375,015 | 12/1887 | Smith | 128/202.12 |
| 476,548 | 6/1892 | Nixon | 128/202.12 |
| 826,029 | 7/1906 | Harper | 128/202.12 |
| 904,172 | 11/1908 | Batter | 128/202.12 |
| 911,528 | 2/1909 | Shoemaker | 128/202.12 |
| 1,224,180 | 5/1917 | Lake | 128/202.12 |
| 1,827,530 | 10/1931 | Le Grand | 128/205.26 |
| 2,373,333 | 4/1945 | Onge | 128/202.12 |
| 3,478,769 | 11/1969 | Zavod et al. | 128/205.26 |
| 4,826,510 | 5/1989 | McCombs | 128/205.11 |
| 4,991,616 | 2/1991 | Fabregat | 128/205.11 |
| 5,061,298 | 10/1991 | Burgoyne, Jr. et al. | 128/205.11 |
| 5,082,471 | 1/1992 | Athayde et al. | 128/205.11 |
| 5,101,819 | 4/1992 | Lane | 128/205.26 |
| 5,133,339 | 7/1992 | Whalen et al. | 128/202.12 |
| 5,188,099 | 2/1993 | Todeschini et al. | 128/202.12 |
| 5,220,502 | 6/1993 | Qian et al. | 128/205.26 |
| 5,229,465 | 7/1993 | Tsuchida et al. | 128/205.11 |
| 5,263,476 | 11/1993 | Henson | 128/205.11 |
| 5,383,448 | 1/1995 | Tkatchouk et al. | 128/203.12 |
| 5,398,678 | 3/1995 | Gamow | 128/205.26 |
| 5,467,764 | 11/1995 | Gamow | 128/202.12 |

FOREIGN PATENT DOCUMENTS

| | | | |
|---|---|---|---|
| 185980 | 7/1986 | European Pat. Off. | 128/205.11 |
| 2837278 | 3/1980 | Germany | 128/205.11 |
| 3274433 | 11/1988 | Japan | 128/205.11 |
| 1274771 | 11/1989 | Japan | 128/205.11 |
| 3052631 | 3/1991 | Japan | 128/205.11 |
| 3097604 | 4/1991 | Japan | 128/205.11 |
| 3131504 | 6/1991 | Japan | 128/205.11 |
| 1223919 | 4/1986 | U.S.S.R. | 128/202.12 |
| 1338862 | 9/1987 | U.S.S.R. | 128/202.12 |
| 1456161 | 2/1989 | U.S.S.R. | 128/205.11 |
| 1680166 | 9/1991 | U.S.S.R. | 128/202.12 |
| 1688873 | 11/1991 | U.S.S.R. | 128/202.12 |
| 1718965 | 3/1992 | U.S.S.R. | 128/202.12 |

OTHER PUBLICATIONS

Textbook of Medical Physiology, Guyton, 6th ed., ©1981, W. B. Saunders Co., Part VIII & IX, pp. 541–558, 128/204.29.
Journal of the A.S.R.E., "Recent Engineering Developments in Strato–Chambers", Bergdoll, Jr., Jan. 1943, pp. 25–33, 128/202.12.

Primary Examiner—Kimberly L. Asher

[57] ABSTRACT

A hypoxic room system for hypoxic training or therapy is provided which simulates oxygen-depleted mountain air. The system employs an oxygen content-reducing device (hypoxicator) which supplies oxygen-depleted air to a hypoxic training room communicating with the device and having ventilating openings for equalizing atmospheric pressure inside the hypoxic room. The system may be applied to interior space inside any structure. The hypoxicator may employ a membrane air-separation principle or a molecular sieve pressure-swing adsorption process.

25 Claims, 4 Drawing Sheets

HYPOXIC ROOM SYSTEM AND EQUIPMENT FOR HYPOXIC TRAINING AND THERAPY AT STANDARD ATMOSPHERIC PRESSURE

RELATED APPLICATION

This application is a continuation in part of the application filed May 22, 1995 by Igor K. Kotliar entitled "Apparatus for hypoxic training and therapy" and given U.S. Ser. No. 08/445,677.

FIELD OF THE INVENTION

The present invention relates to equipment for providing oxygen-depleted air to a user for hypoxic training or therapy whereby a low-oxygen mountain air of different altitudes is simulated, and more particularly, to such equipment which regulates oxygen content and the humidity of the oxygen-depleted air being delivered for non-contact inhaling by a user.

Hypoxic training activates the immune system and protective forces of the organism, and is used for medical, health and fitness purposes. Hypoxic training is a drug-free alternative for treatment and prevention of cardiopulmonary, gastrointestinal, gynecological, skin and ocular diseases, as well as various types of allergy, neurological disturbances, and other diseases. Hypoxic Training is also successfully used for increasing strength, endurance, vitality and resistance to various diseases of healthy people and athletes.

DESCRIPTION OF THE PRIOR ART

European Patent EP 0472 799 AL shows one type of the apparatus for Hypoxic Training on the market. The apparatus employs a powerful compressor to force air through hollow polyfiber membranes in order to provide an oxygen-depleted gas mixture to the user.

This apparatus has a number of disadvantages including excessive weight and noise level and higher than atmospheric pressure of the delivered gas mixture as well. But the main disadvantage of this and other currently available machines is the necessity of sterilization or disposal of the contaminated elements of the respiratory system and the possibility of contamination of the entire system.

The invention presented here is free of these disadvantages and provides for safe multiple use without the need to sterilize any part of the system.

SUMMARY OF THE INVENTION

A principal object of the present invention is to provide equipment for simulating oxygen-depleted mountain air of different altitudes—preferably from 5,000 to 20,000 ft—which is necessary for hypoxic training or therapy.

Another object of the invention is to provide a system for hypoxic training and therapy consisting of a closed room having ventilating openings which communicates with a device which supplies oxygen-depleted air or nitrogen, establishing hypoxic and, if necessary, hypobaric or hyperbaric conditions inside this closed room.

A further object of the invention is to provide a collapsible hypoxic training room which may be installed in any facility and having sufficient ventilation openings in order to automatically maintain normal or hypobaric atmospheric pressure inside.

Yet a further object of the present invention is to provide a device for depleting the oxygen content of the air inside the hypoxic training room employing membrane-separation or molecular sieve-separation principles whereby an oxygen-depleted air is delivered inside a hypoxic training room for a non-contact inhalation.

A further object of this invention is to provide equipment for simulating oxygen-depleted mountain air inside a training or therapy room where the oxygen content, humidity, and temperature of such air can be regulated depending on a training or therapy protocol and a user's condition by means of manual or computerized-logic control.

Another object of this invention is to provide equipment, its installation scheme and a method for establishing hypoxic and optional hypobaric or hyperbaric conditions inside any suitable room or structure with specific ventilation conditions.

A further object of the invention is to provide a system for hypoxic training which includes exercise equipment as its integral part.

Yet another object of the invention is integrating of hypoxic training system inside a motor vehicle or other means of transportation in order to fight drowsiness and increase attentiveness of their operators.

The several embodiments presented here employ varying combinations of equipment for supplying an oxygen-depleted gas mixture for hypoxic training or therapy which requires an air composition preferably with 7% to 15% of oxygen and 93% to 85% of nitrogen.

Each embodiment presented here may be incorporated into an air-conditioning system of any room, building or structure using the systems ventilating ducts and equipment for delivery hypoxic gas mixture.

DESCRIPTION OF THE INVENTION

The object of this invention is to provide equipment which simulates oxygen-depleted mountain air of different altitudes and delivers it to a user for a non-contact inhalation in accordance with a hypoxic training or therapy protocol.

The system consist of two main blocks: a hypoxicator (device for supply oxygen-depleted air or nitrogen with a control unit) and a hypoxic training room which communicate with each other.

Figure 1:
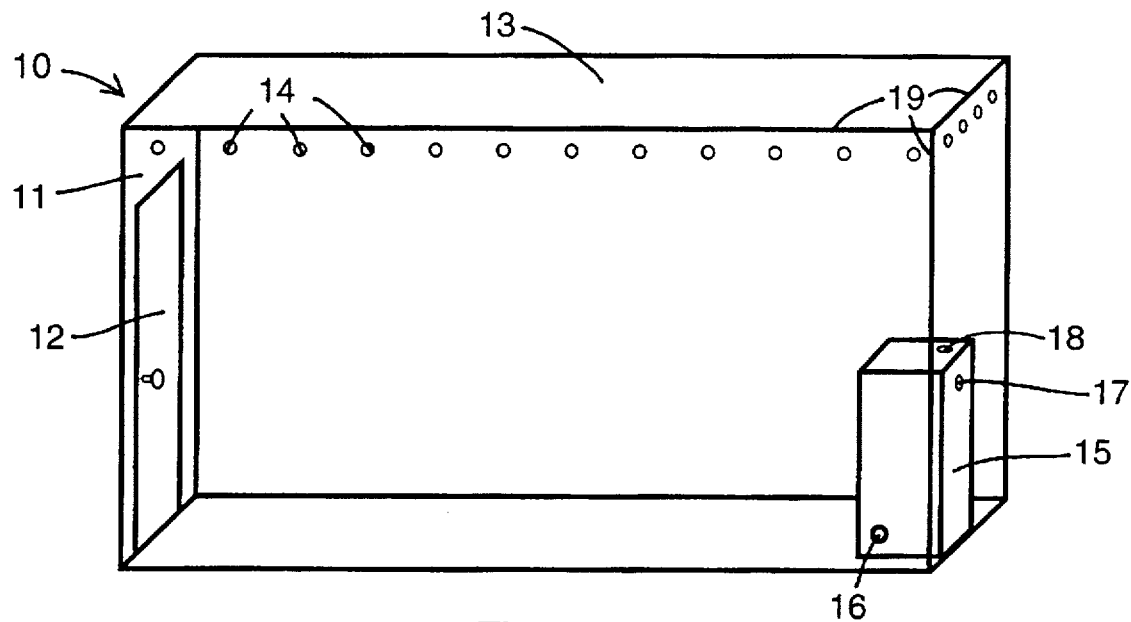
FIG. 1 shows a simplified view of the preferred embodiment and the invention.
Figure 2:
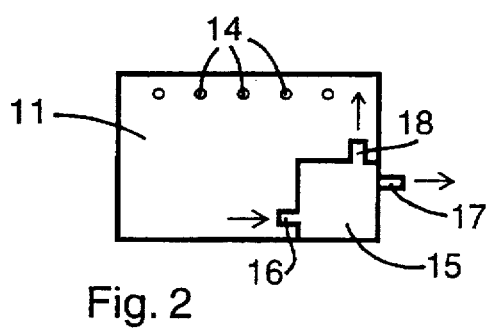
FIG. 2 is schematic view of the preferred embodiment wherein an oxygen-enriched gas mixture is extracted from the system.

FIG. 1 shows a simplified design of a preferred embodiment 10, and FIG. 2 shows a schematic working principle of the same embodiment. A collapsible hypoxic training room 11 having soft or hard walls made preferably from a clear glass or polymer material supported on a metal or plastic framework 19 and equipped with a door 12, a ceiling 13 and an optional floor platform. There are many types of similar rooms marketed currently as "clean room" or "inhalation room" and manufactured by Liberty Industries, Simplex Inc., Clean Room Products Inc., Clestra Cleanroon, Inc. and many other companies. Most of them are suitable for presented here invention and need just a few changes, such as getting ventilating and installation openings.

A hypoxicator 15 employs almost the same working principle as is well-known in medical field membrane-type or molecular sieve-type oxygen concentrators which separate ambient air into oxygen-rich and nitrogen-rich fractions. The main difference between our hypoxicator and an oxygen concentrator is that with an oxygen concentrator, the oxygen-rich gas mixture is used and nitrogen concentrate is released into the atmosphere, and with a hypoxicator, the nitrogen-rich gas mixture is used and the oxygen concentrate is disposed of. The hypoxicator presented in this invention is also several times more productive and does not need a number of elements necessary in oxygen concentrator devices. In this invention we use a custom-made hypoxicator with membrane or molecular-sieve air separation unit being schematically shown in FIGS. 5 and 6 and described later in this document.

The hypoxicator 15 installed inside the hypoxic room 11 draws internal room air through a disposable dust and bacterial filter of intake 16 and separates it into oxygen concentrate disposed through output 17 and nitrogen concentrate being discharged inside room 11 through output 18.

The constant gas mixture withdrawal from room 11 through output 17 causes the same quantities of fresh air to be drawn in through the ventilating openings 14, keeping normal atmospheric pressure inside room 11. The air-flow capacity of openings 14 must be larger than the maximal flow of the oxygen concentrate able to be produced by the hypoxicator 15. It will allow an even atmospheric pressure inside the hypoxic room 11.

The system has a significant advantage—it allows the simulation of hypobaric conditions existing in reality on different altitudes which is important for hypoxic training and therapy. For this purpose, ventilating openings 14 may be equipped with the hypobaric valves allowing to create a necessary pressure difference inside the room 11. In this case it is advisable to reduce the number of openings 14 to one or two of a larger size. These valves (or valve) should be combined with a room pressure monitor and controlled by a computerized control unit which will change the air pressure inside the room 11 in accordance to the oxygen content level allowing perfectly-simulated mauntain air conditions at different altitudes. Suitable low-pressure valves with an extremely sensitive room pressure monitor (model RPM-1) and other necessary accessories are available from MODUS Instruments, Inc.

The performance of the hypoxicator 15 must be enough to lower the oxygen content of the air inside the room 11 to desired level in a desired amount of time. Preferred are those able to produce at least 15 cubic feet (450 liters) per minute of nitrogen concentrate with minimum 90% purity which should be enough for one individual training room. For larger rooms more efficient hypoxicators should be used or a sluice chamber installed at the entrance in order to save energy by frequent door openings. There is no need to make the door, wall and ceiling joins of the hypoxic room 11 absolutely airtight and it may be used without a floor platform as well.

Figure 8:
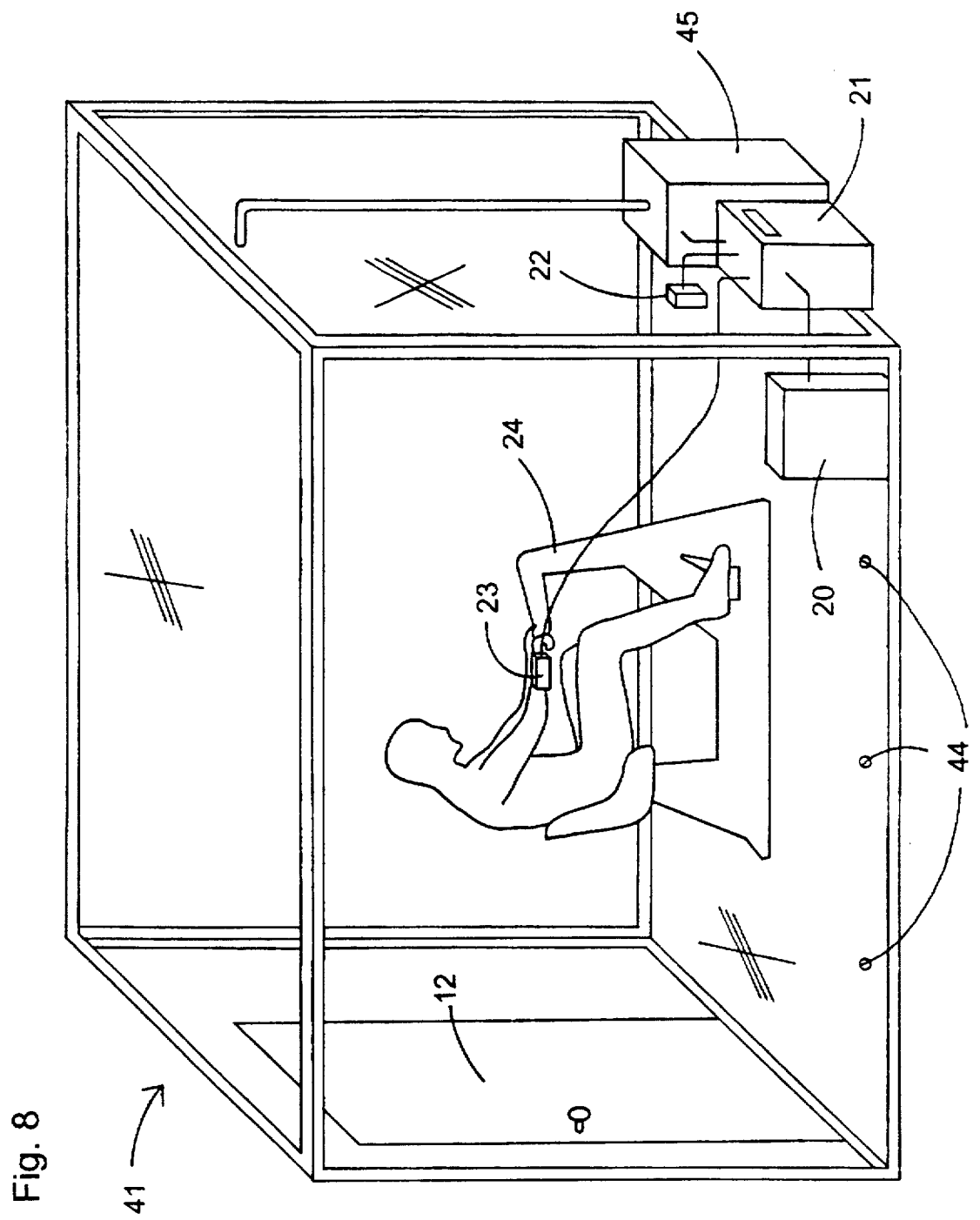
FIG. 8 shows the invented hypoxic room system, including exercise equipment, computerized control unit, humidity and temperature control unit, oxygen sensor and pulse oximeter.

As shown in FIG. 8, the hypoxic room must be equipped with an oxygen-content sensor 22 and an oxygen-depletion alarm 21. Suitable are those manufactured by Micro Switch(a Honeywell Div.), Sensormedics Corp., Servomex, Matheson Gas Products, Enmet Corp. and others.

The oxygen-content sensor constantly measures the oxygen content in the room and transmits the data to a computerized control unit (not shown) which controls the performance of the hypoxicator 45 to achieve and maintain desired air parameters in accordance to training or therapy protocol.

Preferred oxygen content parameters for hypoxic training or therapy lie in the range from 7% to 13% for controlled medical use and 11%–15% for public use for fitness purposes.

It is also necessary for medical purposes to employ a pulse oximeter 23 which measures $SaO_2$—blood saturation with oxygen, preferably finger type. Pulse oximeters manufactured by Nellcor Inc., Edentec, Ohmeda, Puritan-Bennet Corp. and Simed Corp. are suitable.

The oximeter 23 mounted on a finger of a user transmits constantly the pulse rate and $SaO_2$—data to the computerized control 21 unit which chooses the hypoxic parameters most suitable for a user exercising on exercise equipment 24.

A humidity and temperature control unit 20 shown in FIG. 8 may be installed in the system in order to control humidity and temperature inside the room 11.

When the room 11 is in use and the door 12 is closed, the hypoxicator 15 draws the internal room air through the intake 16 returning only the oxygen-depleted gas mixture through the output 18 and discharging the oxygen concentrate through the output 17 outside the room 11. Fresh air is drawn through the ventilating openings 14 equalizing atmospheric pressure inside the room 11 and being mixed with the incoming through the output 18 oxygen-depleted air. The oxygen content level of the air inside the room 11 drops to preset proportions which are maintained by the computerized control unit during the session time in accordance to training or therapy protocol and users conditions.

Another big advantage of the invention presented here is a gradual lowering of the oxygen content of the air inside the hypoxic room during the session which allows a better adaptation to hypoxic condition and eliminates hypoxic shock. A computerized control unit constantly informs a user about the simulated altitude he reaches during a session.

Carbon dioxide produced by a user during a training or therapy session settles because of its higher density and is removed through the low-positioned intake 16 from the room 11. Because of its permeability, which is higher than oxygen and nitrogen, carbon dioxide penetrates faster the oxygen-separating membrane of the hypoxicator 15 and is fully discharged into the atmosphere through the output 17. In case of a molecular sieve-type hypoxicator, carbon dioxide remains with the oxygen concentrate and is removed completely as well.

When the desired oxygen content level is established inside the room 11 and the computerized control unit significantly reduces performance of the hypoxicator 15 the carbon dioxide constantly produced by a user will be always removed first and completely from the room 11.

Excessive moisture will be also removed from the room 11 because of the faster permeability of water vapor through the oxygen separating membrane, but the humidity of the air inside room 11 will be constantly reinstated because of the existance of ventilating openings and kinetic properties of water vapor.

Figure 3:
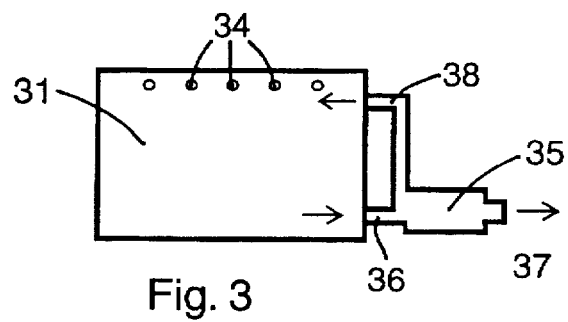
FIG. 3 shows a schematic of an alternate embodiment of the invention with the outside installation of a hypoxicator.

FIG. 3 shows a schematic design of an alternate embodiment 30 which differs from the preferred embodiment only through the outside installation of the hypoxicator 35. The air inside the hypoxic training room 31 is drawn through the intake 36 inside hypoxicator 35 wherein it is separated into oxygen concentrate being disposed through the output 37 and oxygen-depleted gas mixture being returned through the output 38 back into room 31, etc. All other parts and devices are the same as in the preferred embodiment.

Figure 4:
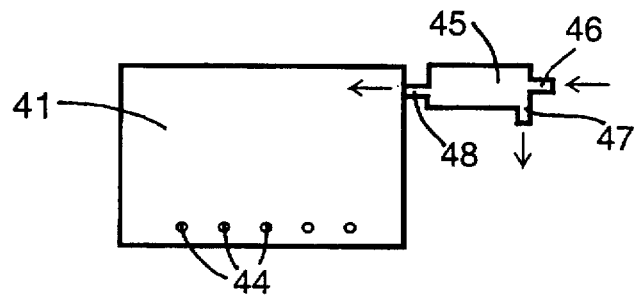
FIG. 4 shows a schematic view of another alternate embodiment of the invention.

FIG. 4 shows a further alternate embodiment 40 wherein the oxygen-depleted air is pumped inside the room 41. The hypoxicator 45 installed preferably outside the room 41 draws outside air through the dust filter of the intake 46 and disposes oxygen-rich gas mixture through the output 47 blowing the oxygen-depleted air into the room 41 through the output 48.

In this embodiment ventilating openings 44 should be installed preferably in the lower portion of the room walls allowing carbon dioxide to be blown out first. The air flow capacity of the ventilating openings 44 must be greater than the volume of the incoming gas mixture by maximal performance of the hypoxicator 45, because it is necessary to keep normal atmospheric pressure inside the hypoxic training room 41.

This alternate embodiment requires a humidifier in order to reinstate the humidity of the incoming dry gas mixture to desired proportions. It is necessary because water vapor is faster than other gases in penetrating an oxygen-separating membrane which makes oxygen-depleted retentate too dry for comfortable use. In case of a molecular sieve separator water vapor is removed with the oxygen concentrate.

The preferred type of humidifier is a disc spray dispenser widely used in air conditioning systems and which can employ the power of the incoming air stream to produce micro-sized water droplets which evaporate instantly. Any other humidifiers available on the market for home or office use are suitable for the invention presented here and may be installed separately inside or outside a hypoxic room. All other parts and equipment are similar to the preferred embodiment. Hyperbaric conditions may be easily established, if necessary, employing hyperbaric valves at the ventilating openings 44 controlled by a room pressure monitor and computerized control unit similar to the preferred embodiment.

Figure 5:
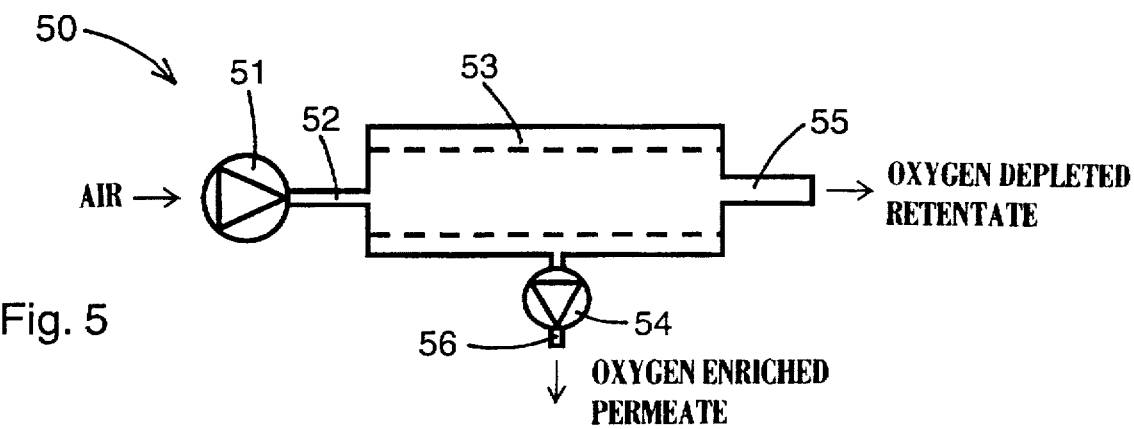
FIG. 5 shows a schematic of a membrane-type hypoxicator.

FIG. 5 shows a schematic design and a working principle of the membrane type hypoxicator 50. A compressor 51 draws an ambient air and supplies compressed air through an outlet 52 into a membrane separation unit 53 wherein it is separated into oxygen rich permeate and oxygen depleted retentate. The permeate is drawn by a vacuum pump 54 being disposed through the outlet 56 and the retentate is discharged through the conduit 55 inside the hypoxic room (not shown).

The system can also work without the vacuum pump 54 being installed here for increasing the efficiency of the separation unit 53. Otherwise, a fan or a blower may be used instead of compressor 50 in which case an efficient vacuum pump 54 is required to achieve the highest air separation grade across the membranes of the separation unit 53.

Most suitable for invention presented here are Thomas WOBL double piston compressors (series 1207 and 2807) and Thomas WOBL piston or rotary vacuum pumps (series TF16, TF25 and 2750) manufactured by Thomas Industries, Inc.

The membrane separation unit 53 is of known construction and may consist of a set of parallel connected membrane cells or a single cell which employ either flat or capillary membranes. The inlet of the separation unit 53 receives compressed air from conduit 52, and separates the air across the membrane and delivers the oxygen-depleted retentate gas through the outlet to conduit 55. The separation results from a pressure difference created by a compressor 50 and/or vacuum pump 54 expelling the oxygen-rich permeate gas mixture as a result of this compressor and vacuum pump arrangement, the retentate gas mixture is delivered further inside a hypoxic room. Similar membrane separation units, usually with hollow-fiber-polymer membranes, are used currently in the medical oxygen-enriching devices.

The best material for the membranes is selected from the group consisting of poly(dimethylsiloxane) also referred to as PDMS or its copolymer, or poly[1-(trimethylsilyl)-1-propyne] also referred to as PMSP, available from the Sanyo Chemical Co., the Matsushita Electric Company or the General Electric Co. Also suitable for use in forming the membranes of the present invention are silicon rubber, natural rubber, carbon, polybutadiene, polystyrene, ethylcelluIlose, butyl rubber, Teflon-FEP, polyvinylacetate, poly(2,6-dimethylphenylene oxide) or poly(methylpentene-1). Suitable for use in forming the membranes are porous polyethylene or polypropylene available from Terumo, Bentley, Johnson & Johnson, Bard, Baxter Travenol, 3M, Shiley or Cope. Other possible materials will be apparent to those skilled in the art, who will be able to substitute equivalent materials for those enunciated here without departing from the invention.

In the preferred embodiment, membrane cells are made with a porous, tubular-shaped support structure having a permeable flat sheet membrane layer on the retentate side of the support structure, the membrane layer being preferably from highly permeable organic, synthetic, ceramic, glass, metal, composite, mineral or biologic material, or combinations thereof in symmetric, asymmetric or composite shape, porous or nonporous. Capillary or hollow-fiber membranes may also be used effectively instead of flat membranes.

Due to their kinetic properties, water vapor, carbon dioxide and oxygen penetrate faster through any kind of membranes than nitrogen, which permits a choice of the most permeable membrane under the lowest possible air pressure in order to increase an efficiency of the membrane separation unit 53.

A humidifier may be connected to hypoxicator 50, if necessary, or installed separately in hypoxic room.

Figure 6:
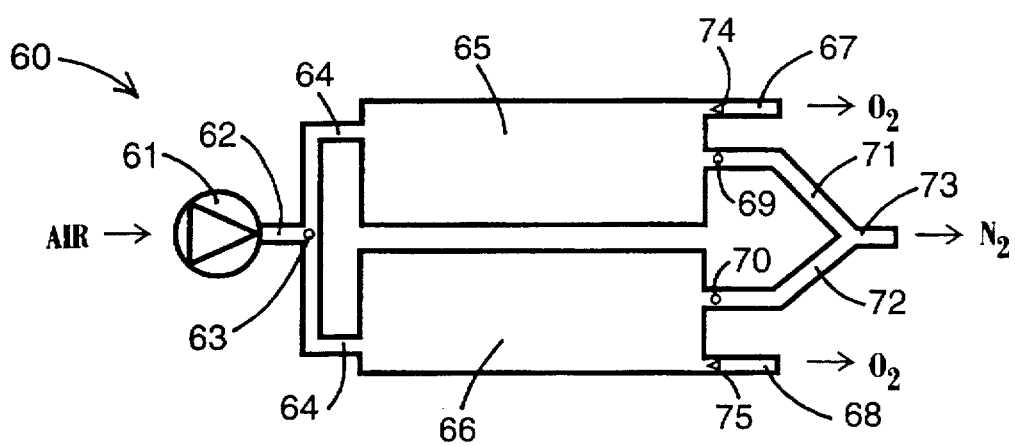
FIG. 6 shows a schematic of a molecular sieve-type hypoxicator.

FIG. 6 shows a schematic design and a working principle of the molecular-sieve type hypoxicator 60 which are almost similar to medical oxygen concentrators being commercialized since mid-1970s and operating on the original Skarstrom cycle.

A compressor 61 draws an ambient air and pressurizes it preferably up to 3 to 10 bar pressure. Compressed air is delivered through the outlet 62, switching valves block 63 and connectors 64 to adsorber bed 65 or adsorber bed 66 alternately. The molecular sieve material adsorbes nitrogen from the compressed air, allowing oxygen and other gases to pass through to disposal outlets 67 and 68.

The two sieve beds 65 and 66 are pressurized alternately in a cyclic manner whereby air flow paths 64 are switched by solenoid switching valves 63. The sieve beds are made preferably from steel used for high-pressure gas containers. As soon as sieve material in adsorber bed 65 becomes saturated with nitrogen a pressurizing valve 69 opens depressurizing bed 65, allowing nitrogen to flow through connector 71 to mixing outlet 73 connected to hypoxic room (not shown here). Some of the oxygen produced at this time by bed 66 is used to purge bed 65 (connections from outlet 68 to bed 65 and from 67 to 66 are not shown here in order to simplify the scheme). At that time sieve bed 66 becomes saturated with the nitrogen and a pressurizing valve 70 opens, allowing depressurization of the bed 66 and the nitrogen being flown through a tube 72 to the mixing outlet 73. The complete cycle is then repeated.

Oxygen disposal outlets 67 and 68 having pressure regulator valves 74 and 75 may join each other, allowing single-tube oxygen transmittion to a wasting point.

The performance of compressor 60 is controlled by a manual or computerized control unit constantly receiving data from an oxygen content sensor, oximeter and other electronic sensors inside a hypoxic room.

The particulary preferred materials for adsorbing nitrogen are molecular-sieve zeolites or crystalline aluminosilicates of alkali earth elements, both synthetic and natural, and Molecular-Sieve Carbon, type CMSO2, available from Calgon Corp., Bergbau-Forschung GmbH in Germany and Takeda Chemical Company in Japan. Organic zeolites, pillared interlayer clays (PILCS) and other suitable molecular sieve materials may also be used.

The productivity of the hypoxicator in this embodiment should preferably be in a range from 30 to 50 liters per minute of oxygen with 80% to 90% purity which will allow establishing of 12% $O_2$ hypoxic conditions in a 5 cubic meters (185 cubic feet) training room in approximately 10 to 20 minutes.

The most suitable compressor for this embodiment is the Thomas WOBL piston compressor. A humidifier may be connected to hypoxicator 60, if necessary, or installed separately in hypoxic room.

Figure 7:
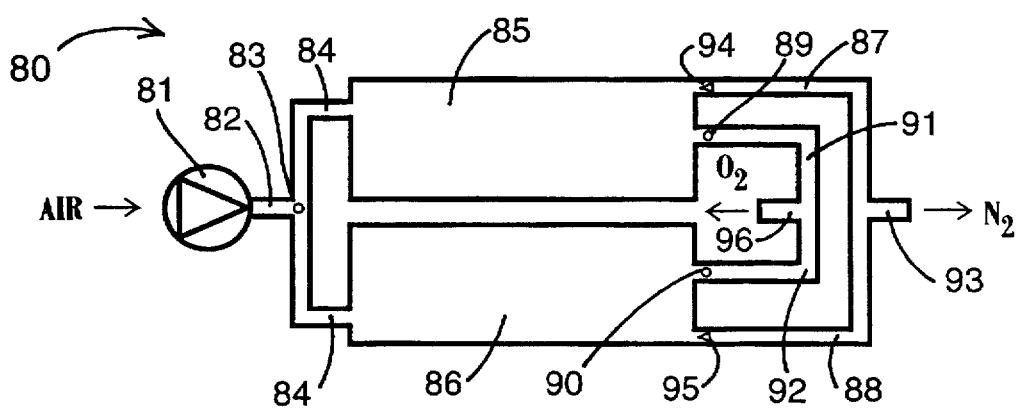
FIG. 7 shows a schematic view of an alternate molecular sieve-type hypoxicator.

FIG. 7 shows a scheme of a most efficient embodiment of hypoxicator 80 employing preferably Molecular Sieve Carbon type CMSN2 in a pressure-swing adsorption system which allows to produce nitrogen with up to 99.9% purity and absolutely free from carbon dioxide.

Compressor 81 supplies air pressurized preferably up to 3 to 10 bar through the outlet 82, switching valves block 83 and connectors 84 to molecular sieve beds 85 and 86. Each sieve bed is alternately pressurized in a cyclic manner and supplies nitrogen until it becomes saturated with oxygen. Bed 85 is pressurized by closing a pressurizing valve 89 and adsorption process begins. Oxygen and carbon dioxide are adsorbed by the adsorbent and nitrogen flows through the pressure regulator valve 94 and conduit 87 to mixing outlet 93 connected to hypoxic room (not shown). When adsorbent in the bed 85 becomes saturated with oxygen a solenoid valve 83 switches the flow path of the compressed air to bed 86 which is pressurized by closing pressurizing valve 90.

At the same time, the bed 85 is depressurized by opening valve 85, allowing oxygen to escape from the adsorbent and to be disposed through the conduit 91 and outlet 96. At that time, the adsorbent in the sieve bed 86 becomes saturated with oxygen and valve 83 switches air flow path to bed 85 which is pressurized by closing valve 89. The complete cycle is then repeated.

One, three or four-bed adsorbing units may be made using the same principle, if necessary. CMSN2 is also available from Bergbau-Forshung GmbH and Takeda Chemical Company. Zeolites made of organic materials are also suitable. Under normal operating conditions, the molecular sieve is completely regenerative and will last indefinitely.

The Thomas piston compressors are most suitable for this embodiment. A humidifier may be connected to hypoxicator 80 or installed separately in hypoxic room. All necessary switches, valves, pressure regalators, manometers, pressure display-controllers and transmitters, filters, fittings and tubing are available from Modus Instruments, Inc., Victor Equipment Company and AirSep Corporation.

The invented system could be applied to any closed room or structure, such as a patient room in a hospital, residential rooms, fitness club rooms, office and conference rooms, schools and child care facilities, theatres, cinemas, restaurants and even a room inside a motor vehicle or other means of transportation. Two basic conditions must be met to build a system are sufficient ventilation of the room allowing instant reinstating of the atmospheric pressure inside the room and a safe disposal of oxygen. For instance, a hypoxicator may be installed as shown in FIGS. 1–4 inside or outside a fitness room having a sufficient ventilation through the door or window.

Figure 9:
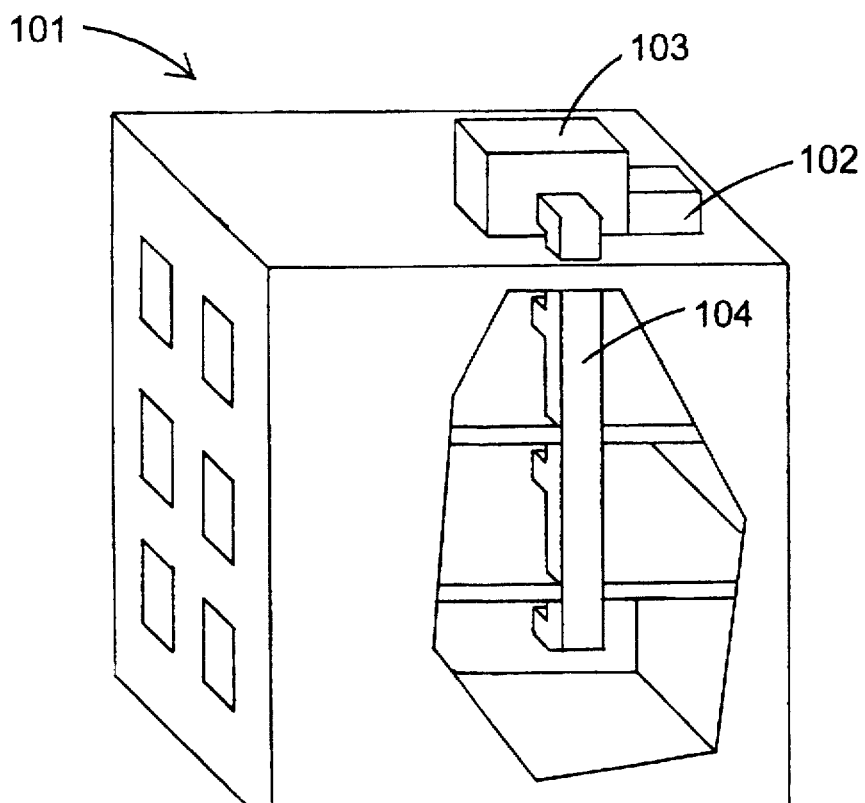
FIG. 9 shows a simplified view of a building with a hypoxicator incorporated into an air conditioning system of the building.

As shown in FIG. 9, the hypoxic room system may be easily integrated into any air conditioning system 103 of any building or structure 101 using existing ventilation ducts 104 and equipment 102 for delivery hypoxic gas mixture to any floor or room in the building. This will improve peoples state of health, increase their productivity and lower medical expenses. A hypoxicator may be incorporated into any separate room air conditioner.

Figure 10:
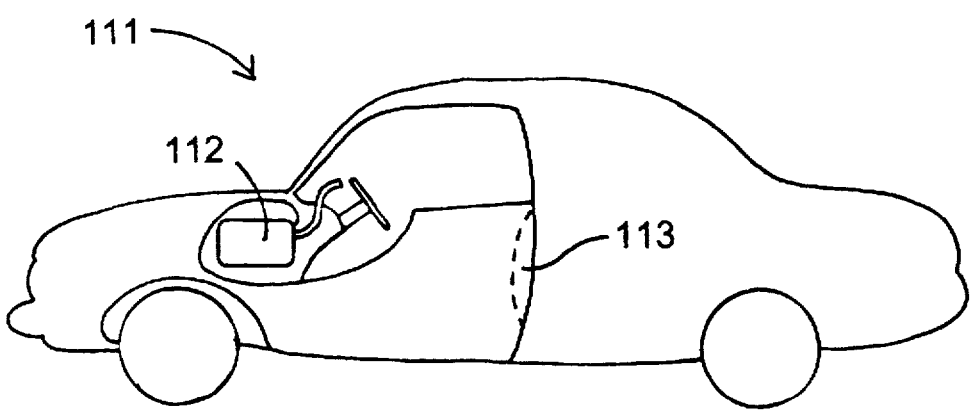
FIG. 10 shows a simplified view of a car with a hypoxicator incorporated behind a dashboard.

The installation scheme of FIG. 4 makes the system most suitable and safe for use in a passenger car 111 or other motor vehicles with a closed passenger space as shown in FIG. 10. Since most of Americans waste hours of their active life every week inside a car some of this time could be used to their advantage—for hypoxic training.

A small, preferably 12V/DC-powered hypoxicator 112 with membrane or molecular sieve type separation principles described earlier may be installed inside a car interior or behind a dashboard. There is also enough space inside or under passenger seats. A hypoxicators delivery system may be also integrated in a ventilating system. Two conditions must be met in this embodiment in order to create an invented hypoxic room system: an outside air must be drawn for separation and an oxygen concentrate must be discharged outside a car 111. There are many openings in a car body sufficient to play a role of ventilating openings 44 and constantly equalizing air pressure in a car interior with the outside atmospheric pressure and, if necessary more openings could be made, preferably at doorjambs 113.

The lowest oxygen content of the supplied gas mixture should be preferably 13%–15% by maximal hypoxicators performance which is absolutely safe and unnoticable by a user and even may be used for fighting sleepiness and increasing attentiveness and vitality. In case of a membrane-type hypoxicator it is simple to preset the performance of the separation unit for a steady supply of the air with 13–15% of oxygen.

In case of a molecular sieve adsorption separator, the produced nitrogen should be mixed with the fresh air in proportion 1:2.5 which makes the air with exactly 15% of oxygen. The mixing must be safe and automatically which may be achieved by transmitting nitrogen through "Y"- shaped mixing adapter with a larger fresh air intake opening, allowing 2.5 times more ambient air than nitrogen to be automatically sucked into the system for mixing. This and a computerized control unit with the oxygen-depletion alarm will insure the safety of the system for hypoxic training inside a car.

The installation scheme shown on FIG. 2 is also suitable for closed-type motor vehicles. In this case, car ventilation ducts and other car body openings play the role of ventilation openings 14. An oxygen concentrate may be discharged to outside through any specially made opening for outlet 17. The best place for incorporating outlet 17 is an outside mirror supporting structure because it communicates with the a car interior through the mirror adjustment mechanism wherein a connection tubing should be installed inside the mirror supporting structure ending with a specially made opening outside and with the connector at inner panel of the door for hypoxicators outlet 17.

An inhalation mask with hypoxic air supply tubing retractable from a dashboard or other interior part may be also installed for individual hypoxic training inside a motor vehicle. In this case a mask should be preferably handheld, without any straps, which is safer. This application is most beneficially for a long-distance truck drivers or train operators. A motorist, feeling drowsy, could take a 3-5 minute session of hypoxic inhalation which will significantly increase his cardiopulmonary activity, attention and vitality.

Car manufacturers could easily integrate this invention in a ventilating system of a vehicle as an additional luxury feature. The presented here invention may be marketed as an anti-sleep mode device for operators of any means of transportation. The system can switch on automatically if a user wears on a finger or another body part a pulse oximeter connected to a computerized or fuzzy logic control unit. When a pulse rate of a user drops to the lowest for this individual level a system will be switched on automatically and hypoxic conditions will be established for a time, necessary to increase user activity to desired level. A blood saturation with oxygen is also under constant control.

A big advantage of the invented system for this application is that it does not disturb a user and does not cause a "panic effect" which is genetically preset in humans if a part of the oxygen in the air is replaced by carbon dioxide. The system may be successfully used for hypoxic training of mammals as well.

What is claimed is:

1. A system for use in an external atmospheric environment of air at an external ambient air pressure and having an ambient oxygen concentration for providing a reduced-oxygen atmosphere to a user, said system comprising:

a gas separation device having an inlet intaking an intake gas mixture and first and second outlets, said first outlet transmitting a first gas mixture derived from said intake gas mixture and having a higher oxygen content than the intake gas mixture and said second outlet transmitting a second gas mixture derived from said intake gas mixture and having a lower oxygen content than the intake gas mixture;

a breathing chamber having an internal space therein containing air and including an entry communicating with said internal space and through which the user can enter said internal space;

said second outlet communicating with said internal space and transmitting said second mixture to said internal space so that said second mixture mixes with the air in the internal space;

said first outlet transmitting said first gas mixture to the external atmospheric environment; and said breathing chamber permitting the communication of air in at least one direction between the external atmospheric environment and the internal space and in combination with the gas separation device, maintaining the air in the internal space at a pressure generally equalized with the ambient air pressure of the external atmospheric environment and at a substantially constant concentration of oxygen substantially lower than said external ambient oxygen concentration.

2. The invention according to claim 1 and said inlet of said gas-separation device intaking the intake gas mixture from the air in said space.

3. The invention according to claim 1 and said inlet of said gas-separation device intaking the intake gas mixture from the air of said external atmospheric environment.

4. The invention according to claim 1 and said breathing chamber having vents therein, said vents providing for flow of air between said external atmospheric environment and said internal space.

5. The invention according to claim 4 and said vents having apertures therein through which air can flow in either direction between said internal space and said external atmospheric environment.

6. The invention according to claim 1 and the air in the internal space having an oxygen concentration of about 7 to 11%.

7. The invention according to claim 1 and exercise equipment for training of said user in said internal space of said breathing chamber.

8. The invention according to claim 7 wherein said user is a non-human mammal.

9. The invention according to claim 1 and the air in the internal space having an oxygen concentration of about 11 to 15%.

10. The invention according to claim 1 and said entry having a doorjamb structure defining an entry opening in the chamber through which the user can enter the chamber and a door covering said opening, the doorjamb structure permitting passage of air between the internal space and the external environment.

11. A system for use in an external atmospheric environment of air at an external ambient air pressure for providing a low-oxygen environment for a user, said system comprising:

a chamber comprising a door and wall structure defining a closed space into which the user can enter through the door;

a gas processing device having an intake and first and second outlets, said device intaking a gas mixture through said intake and emitting a reduced oxygen gas mixture having a lower concentration of oxygen than said gas mixture through said first outlet and emitting an enriched-oxygen gas mixture having a greater concentration of oxygen than said gas mixture through said second outlet;

said first outlet being connected with said chamber so that the reduced-oxygen gas mixture is emitted into said closed space inside the chamber and mixes with the air therein;

said chamber having apertures therein allowing communication therethrough of air in the outside environment with air in the chamber, said chamber and said gas processing device maintaining the air in the closed space at a pressure substantially equal to the external ambient air pressure and at a substantially constant oxygen concentration lower than the air outside the chamber;

said gas processing device comprising a separation unit to which the intake gas mixture from the inlet is transmitted, said separation unit separating the intake gas mixture into a reduced oxygen gas mixture with an oxygen concentration lower than said intake gas mixture and an enriched oxygen gas mixture with an oxygen concentration higher than said intake gas mixture, said separation unit having a reduced oxygen mixture conduit through which said reduced oxygen gas mixture is transmitted and an enriched oxygen mixture conduit through which said enriched oxygen gas mixture is transmitted;

said first outlet being operatively associated with said reduced oxygen mixture conduit and receiving said reduced oxygen gas mixture therefrom, said second outlet being operatively associated with said enriched oxygen mixture conduit and receiving said enriched oxygen gas mixture therefrom and releasing said enriched oxygen gas mixture to the external atmospheric environment.

12. The invention according to claim 11 and said separation unit comprising a housing defining a space therein and having a separating membrane supported therein dividing the space into a retentate space and a permeate space, and a pump pumping said intake gas mixture across said membrane and said intake gas mixture to be separated thereby into oxygen enriched permeate in said permeate space which is transmitted to said second outlet and oxygen depleted retentate in said retentate space which is transmitted to said first outlet and released inside said chamber.

13. The invention according to claim 11 and said separation unit comprising a pump applying said intake gas mixture to a pressure swing adsorption device having molecular sieve material which adsorbs nitrogen from the intake gas mixture being compressed by said pump, leaving the enriched oxygen gas mixture which is transmitted to said enriched oxygen conduit and is discharged to the external atmospheric environment outside said chamber and said adsorption device on depressurization releasing a nitrogen concentrate gas which is transmitted as said reduced oxygen gas mixture to said reduced oxygen conduit and is released into said chamber.

14. The invention according to claim 11 and said separation unit comprising a pump applying said intake gas mixture to a pressure swing adsorption device having molecular sieve material which adsorbs oxygen from the intake gas mixture being compressed by said pump leaving the reduced oxygen gas mixture which is transmitted to said reduced oxygen conduit and released into said chamber and said adsorption device on depressurization releasing an oxygen concentrate gas which is transmitted as said enriched oxygen gas mixture to said enriched oxygen conduit and is discharged to the outside environment.

15. The invention according to claim 11 and said intake communicating with said closed space inside the chamber so that the intake gas mixture is drawn from the air in the chamber.

16. The invention according to claim 15 and said apertures in said chamber being located in an upper portion of the chamber.

17. The invention according to claim 11 and said intake intaking the intake gas mixture from the air of the external atmospheric environment outside the chamber.

18. The invention according to claim 17 and said apertures in said chamber being located in a lower portion of the chamber.

19. The invention according to claim 11 and said apertures providing openings in said wall structure.

20. The invention according to claim 11 and said chamber being part of a vehicle and said user being an operator of said vehicle;

said system selectively supplying a hypoxic environment to said operator so as maintain the alertness of said operator.

21. A system for hypoxic training and therapy simulating an oxygen-depleted mountain air of a higher altitude, said system comprising:

a structure defining a closed space therein, said structure having a door and ventilating openings through which air can pass so that air in the closed space and air outside said structure remain at substantially equal pressures;

an oxygen content-reducing device separating an intake air mixture drawn from said air outside said structure into an oxygen concentrate and a nitrogen concentrate;

said oxygen content-reducing device transmitting said nitrogen concentrate through an outlet communicating with said closed space and causing said air in said closed space to be reduced in oxygen content relative to the air outside the structure, said device transmitting said oxygen concentrate through a second outlet to a location outside said structure;

a control unit controlling the operation of said oxygen content-reducing device;

an oxygen content sensor monitoring an oxygen content level inside said closed space and communicating with said control unit so that the oxygen content of the air in the closed space is maintained at a substantially constant desired level.

22. The invention according to claim 21 and said system having a humidity and temperature control unit regulating humidity and temperature of the air inside said closed space.

23. The invention according to claim 21 and said system having a pulse oximeter monitoring the user's pulse rate and blood saturation with oxygen; said oximeter transmitting data to said control unit; and said control unit regulating the oxygen content of the air in the closed space responsive to said data.

24. The invention according to claim 21 and physical exercise equipment inside said closed space.

25. The invention according to claim 21 and said structure defining said closed space being a part of a building, and said oxygen content-reducing device is incorporated into an air-conditioning system of said building and using ventilation ducts of the building for delivery of said nitrogen concentrate to said closed space.

* * * * *

(12) EX PARTE REEXAMINATION CERTIFICATE (10058th)
United States Patent
Kotliar

(10) Number: US 5,799,652 C1
(45) Certificate Issued: Feb. 27, 2014

(54) HYPOXICO ROOM SYSTEM AND EQUIPMENT FOR HYPOXIC TRAINING AND THERAPY AT STANDARD ATMOSPHERIC PRESSURE

(75) Inventor: Igor K. Kotliar, New York, NY (US)

(73) Assignee: Hypoxico Inc., New York, NY (US)

Reexamination Request:
No. 90/012,354, Jun. 14, 2012

Reexamination Certificate for:
Patent No.: 5,799,652
Issued: Sep. 1, 1998
Appl. No.: 08/505,621
Filed: Jul. 21, 1995

Related U.S. Application Data

(63) Continuation-in-part of application No. 08/445,677, filed on May 22, 1995, now Pat. No. 5,850,833.

(51) Int. Cl.
*A63B 23/18* (2006.01)
*A62B 7/00* (2006.01)
*A62B 9/00* (2006.01)
*G05B 1/00* (2006.01)

(52) U.S. Cl.
USPC ............ 128/205.11; 128/200.24; 128/202.12; 128/205.26; 482/13

(58) Field of Classification Search
USPC ....................... 128/202.12, 205.26
See application file for complete search history.

(56) References Cited

To view the complete listing of prior art documents cited during the proceeding for Reexamination Control Number 90/012,354, please refer to the USPTO's public Patent Application Information Retrieval (PAIR) system under the Display References tab.

*Primary Examiner* — Matthew C. Graham

(57) ABSTRACT

A hypoxic room system for hypoxic training or therapy is provided which simulates oxygen-depleted mountain air. The system employs an oxygen content-reducing device (hypoxicator) which supplies oxygen-depleted air to a hypoxic training room communicating with the device and having ventilating openings for equalizing atmospheric pressure inside the hypoxic room. The system may be applied to interior space inside any structure. The hypoxicator may employ a membrane air-separation principle or a molecular sieve pressure-swing adsorption process.

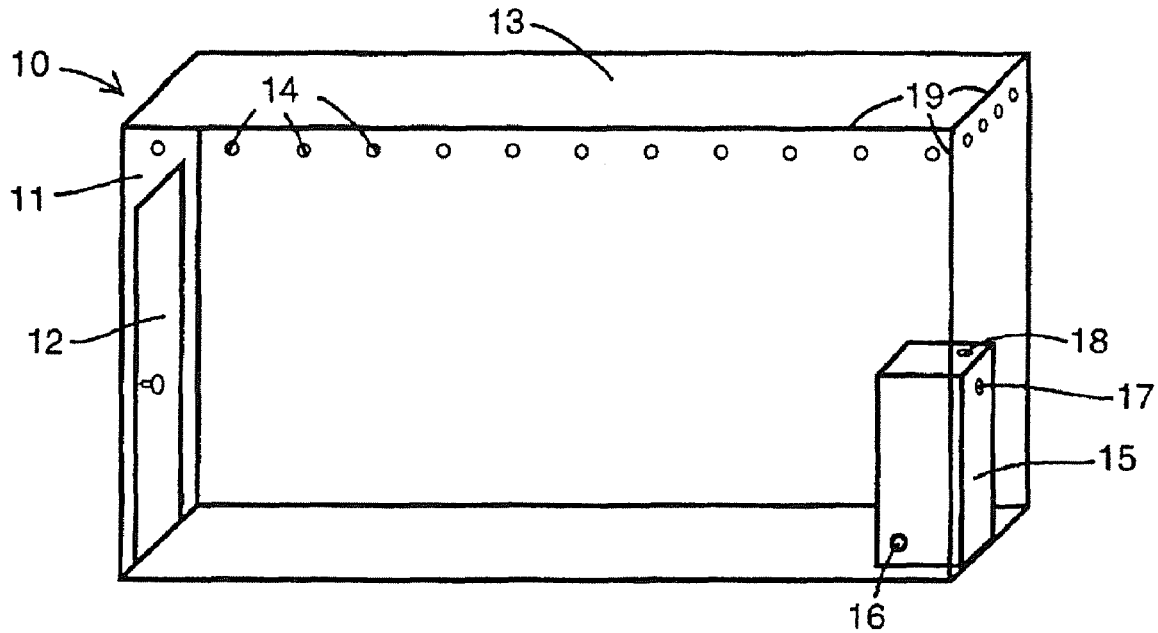

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-25 is confirmed.

* * * * *